US010206560B2

(12) United States Patent
Kindler (10) Patent No.: US 10,206,560 B2
(45) Date of Patent: Feb. 19, 2019

(54) SHANK FOR A FLEXIBLE ENDOSCOPE OR A FLEXIBLE ENDOSCOPIC INSTRUMENT

(71) Applicant: Karl Storz SE & Co. KG, Tuttlingen (DE)

(72) Inventor: Gereon Kindler, Schaffhausen (CH)

(73) Assignees: Karl Storz SE & Co. KG, Tuttlingen (DE); Storz Endoskop Produktions GmbH, Tuttlingen (DE)

( * ) Notice: Subject to any disclaimer, the term of this patent is extended or adjusted under 35 U.S.C. 154(b) by 872 days.

(21) Appl. No.: 14/013,366

(22) Filed: Aug. 29, 2013

(65) Prior Publication Data

US 2014/0073855 A1    Mar. 13, 2014

(30) Foreign Application Priority Data

Aug. 31, 2012  (DE) .......................... 10 2012 108 076

(51) Int. Cl.
*A61B 1/00* (2006.01)
*A61B 1/005* (2006.01)
*A61B 17/00* (2006.01)

(52) U.S. Cl.
CPC .......... *A61B 1/0055* (2013.01); *A61B 1/0016* (2013.01); *A61B 1/0057* (2013.01); *A61B 17/00234* (2013.01); *A61B 1/0056* (2013.01)

(58) Field of Classification Search
CPC ... A61B 1/0057; A61B 1/0051; A61B 1/0052; A61B 1/0125
USPC ................................................ 600/146, 149
See application file for complete search history.

(56) References Cited

U.S. PATENT DOCUMENTS

| 4,203,430 A | 5/1980 | Takahashi |
| 4,982,725 A | 1/1991 | Hibino et al. |
| 5,531,664 A * | 7/1996 | Adachi et al. ................ 600/149 |
| 2004/0097791 A1 | 5/2004 | Tokuda et al. |
| 2005/0131279 A1 | 6/2005 | Boulais et al. |
| 2008/0183128 A1 | 7/2008 | Morriss et al. |
| 2010/0036202 A1* | 2/2010 | Lin et al. ...................... 600/146 |
| 2010/0069712 A1* | 3/2010 | Yamaya ........................ 600/107 |
| 2011/0295242 A1 | 12/2011 | Spivey et al. |
| 2013/0102960 A1* | 4/2013 | Miyoshi .................... 604/95.04 |

FOREIGN PATENT DOCUMENTS

| DE | 2914748 A1 | 10/1979 |
| DE | 69333140 T2 | 6/2004 |
| EP | 0612496 A1 | 8/1994 |
| EP | 1902665 A1 | 3/2008 |
| EP | 2189103 A1 | 5/2010 |

(Continued)

*Primary Examiner* — Alexandra L Newton
*Assistant Examiner* — Rynae Boler
(74) *Attorney, Agent, or Firm* — Whitmyer IP Group LLC (57) ABSTRACT

A shank for a flexible endoscope or for a flexible endoscopic instrument includes a first shank portion and, a second shank portion, angled relative to a distal end region of the first shank portion by a longitudinal adjustment of at least one tensioning means which is guided in a longitudinally displaceable manner inside the second shank portion and connected to a distal end region of the second shank portion. The longitudinal adjustment by least one threaded drive, which can be driven by at least one torsion shaft extending inside the first shank portion. The invention also relates to a flexible endoscope and a flexible endoscopic instrument.

20 Claims, 3 Drawing Sheets

(56) References Cited

FOREIGN PATENT DOCUMENTS

| JP | H0482529 A | 3/1992 | | |
|---|---|---|---|---|
| JP | H07134253 A | 5/1995 | | |
| WO | WO-2012/132636 | * | 10/2012 | ............... A61B 1/00 |

* cited by examiner

SHANK FOR A FLEXIBLE ENDOSCOPE OR A FLEXIBLE ENDOSCOPIC INSTRUMENT

FIELD OF THE INVENTION

The present invention relates to a shank for a flexible endoscope or for a flexible endoscopic instrument, and to a flexible endoscope and a flexible endoscopic instrument having such a shank.

BACKGROUND OF THE INVENTION

Flexible endoscopes are used for many applications in medicine and technology. Flexible endoscopes of this kind comprise a flexible elongate shank, which is suitable for insertion into a cavity, for example a cavity inside the body or a cavity of a technical object. Generally, an endoscope lens is arranged at the tip of the endoscope shank to generate an image of a scene in the observed cavity. To record and transmit the endoscopic image from the distal end region (i.e. remote from the observer) to the proximal end region (i.e. near the observer) of the endoscope, it is possible, for example, to provide a coherent bundle of optical fibers extending inside the shank, or else an electronic image recorder, for example a CCD chip, which is arranged in the region of the distal end of the shank, and the signals of which are transmitted to the proximal end region via electrical lines extending inside the shank. Since there is generally insufficient light in the observed cavity, a light-guiding system can also be arranged inside the shank in order to convey light to the distal end of the endoscope, where it is used to illuminate the cavity. Furthermore, the endoscope shank can have one or more working channels through which endoscopic work instruments are passed from the proximal to the distal end region of the shank, and with the aid of which manipulations can be performed inside the cavity.

Endoscopic instruments are also known that comprise a flexible elongate shank which is likewise suitable for insertion into a cavity, for example a cavity inside the body or a cavity of a technical object. A flexible endoscopic instrument of this kind can be used to perform manipulations in the cavity and, for this purpose, can be designed for example as a grasping instrument for gripping and manipulating tissue or articles in the cavity inside the body or in the cavity of a technical object. For this purpose, a tool is arranged at the distal end of the flexible shank and can be operated from the direction of the proximal end of the shank by way of a transmission means extending inside the shank. A flexible endoscopic instrument of this kind generally does not have a dedicated optical unit for recording an endoscopic image, but it can in particular be used together with a flexible endoscope.

It is often desirable to be able to angle the distal end of the shank, i.e. the tip of the endoscope or of the endoscopic instrument, in order to make insertion of the endoscope or of the endoscopic instrument through a non-rectilinear channel easier, in order to be able to move the tip in a lateral direction inside a cavity, and in order to be able to vary the viewing direction of an optical unit arranged in the endoscope tip or the working direction of a tool arranged at the tip of the endoscopic instrument. For this purpose, the shank has a controllable portion, in particular a controllable end portion, that can be actively angled by a desired amount in a desired direction and, for this purpose, can be controlled from the direction of the proximal end of the endoscope or of the endoscopic instrument. The shank for a flexible endoscopic instrument does not itself need to have a tool and a transmission means, but instead can comprise, for example, a working channel into which a flexible endoscopic work instrument, which cannot be actively angled and which has such a tool, can be inserted as far as the distal end of the shank and optionally beyond this, such that the flexible work instrument can be angled with the aid of the shank.

To permit controllable angling of a portion of a shank of a flexible endoscope, it is known to design this with a base structure composed of individual, mutually pivotable segments that can be actuated by cable pulls or Bowden cables guided in the endoscope shank. For actuation, hand wheels in particular that are arranged on the handgrip of the endoscope are provided. According to US 2005/0131279 A1, each segment of a controllable portion of the endoscope shank is mounted so as to be pivotable relative to the next and/or preceding segment. To angle the shank portion in question or the endoscope tip, four cable pulls are provided which are guided as far as the endoscope tip from a control apparatus arranged at the proximal end. The cable pulls extend in the edge region of the segments and are offset in each case by 90° to each other relative to a longitudinal axis, such that control of the endoscope tip to a desired direction can be brought about by rolling up the corresponding cables in the control apparatus.

However, the cables of such cable pulls have a tendency to lengthen after repeated use, which adversely affects the controllability of the endoscope tip or makes it necessary to regularly re-tension the cable pulls. Resetting devices for setting the tension of the cable pulls are known, for example from DE 29 14 748 C2 and U.S. Pat. No. 4,203,430; however, resetting devices of this kind are associated with increased outlay in terms of construction and control. The necessary permanent tensioning of the cable pulls can also lead to a shortening of the shank, which can have an adverse effect on the controllability of the endoscope tip and indeed the properties of the endoscope shank, for example the flexibility or surface quality. The attainable angling also depends on the curvature of the whole shank portion through which the cable pulls are guided, with the result that there is no clear relationship between the position of a hand wheel, with which a cable pull can be rolled up, and the attained deflection angle of the endoscope tip. Curvatures of the endoscope shank also cause increased friction of the cable pulls, which likewise makes it difficult to control the angling. Finally, the cable pulls, particularly in longer shanks, may sever on account of the friction and of corresponding wear.

JP 07134253 A discloses an endoscope with a curvable portion comprising a plurality of segments which are interconnected in a hinged manner and which have threaded nuts, the latter cooperating with bolts that are connected to a flexible shaft. Near a proximal end of the curvable portion, a micromotor is arranged in the shank of the endoscope and sets the flexible shaft in rotation in order to control angling of the curvable portion. This entails quite a considerable outlay in terms of construction. Moreover, the load-bearing capacity of the shaft with the associated threaded nuts is not always sufficient. In addition, arranging a micromotor in an endoscope shank of small diameter, inside which there extend further lines and channels, is not readily possible, and it is also associated with considerable effort for reasons of accessibility to the motor for repair and maintenance purposes and, if appropriate, for cleaning and sterilization.

SUMMARY OF THE INVENTION

It is the object of the present invention to specify a shank for a flexible endoscope or for a flexible endoscopic instrument, and also a flexible endoscope and a flexible endoscopic instrument, in which the aforementioned disadvantages are avoided and wherein the shank, in particular, can be controlled precisely and has a simple design, is permanent and robust.

This object is achieved by a shank for a flexible endoscope, and a flexible endoscopic instrument.

A shank according to the invention for a flexible endoscope or for a flexible endoscopic instrument is elongate and is designed for insertion into a cavity, for example a cavity inside the body or a cavity of a technical object. The flexible endoscope can in particular comprise a handgrip, which is arranged at a proximal end of the shank and can have control elements and/or connections for further instruments, for example a suctioning and flushing device, a light source or a camera unit. The handgrip can also contain a camera. The flexible endoscopic instrument can in particular have a handgrip arranged at a proximal end of the shank with an actuating element for a tool arranged at the distal end of the shank. The flexible endoscope or the flexible endoscopic instrument is in particular designed for use in medical procedures, particularly in surgical procedures, or for technical applications.

The shank comprises a first shank portion and, arranged in the distal direction from the first shank portion, a second shank portion, which can in particular adjoin a distal end region of the first shank portion. The shank can comprise further shank portions. The second shank portion can be designed, for example, as an endoscope tip that can be angled. The second shank portion can be angled relative to the distal end region of the first shank portion. In particular, the second shank portion is designed to be actively curvable, while the first shank portion is at least partially flexible but not actively curvable.

Inside the second shank portion, at least one tensioning means is arranged that acts in the longitudinal direction of the second shank portion. Here, the term "tensioning means" comprises, for example, a wire or a cable pull that exerts a tensile force, but it can also be designed as a pushing means, for example as a flexible rod or as a rigid wire or else as a wire guided in a sleeve, for example as a Bowden cable, which is suitable for transmitting both pulling and also pushing forces in the longitudinal direction of the second shank portion. The second shank portion can be angled relative to a distal end region of the first shank portion by a longitudinal adjustment of the tensioning means. To this end, the tensioning means is guided in a longitudinally displaceable manner inside the second shank portion and connected to a distal end region of the second shank portion. In particular, the tensioning means cooperates with a support structure of the second shank portion in such a way that a change in length or a longitudinal displacement of the tensioning means causes an angling of the second shank portion, in particular a curving of the second shank portion. The tensioning means can be guided from a proximal end region to a distal end region of the second shank portion in particular and can be connected to the support structure in the distal end region only. The support structure can consist, for example, of a sequence of segments connected to one another in a hinged manner, wherein the tensioning means, laterally offset with respect to the hinges, engages on at least one end segment of the support structure.

According to the invention, at least one threaded drive is arranged for the longitudinal adjustment of the at least one tensioning means. To this end, the threaded drive can for example be part of the tensioning means or engage on the latter. By way of example, a threaded drive comprises a threaded rod with a male thread and a nut with a corresponding female thread, which cooperate in such a way that a rotation of the nut relative to the threaded rod displaces the threaded rod relative to the nut in the longitudinal direction of the threaded rod in order to cause a longitudinal adjustment of the tensioning means.

The at least one threaded drive arranged for the longitudinal adjustment of the at least one tensioning means can be driven by at least one torsion shaft extending inside the first shank portion. The torsion shaft arranged in the first shank portion can transmit an actuation movement, generated by actuation means arranged in the proximal direction from the first shank portion, to the at least one threaded drive, which can be arranged, for example, in the second shank portion or in an end region of the first shank portion, in order to drive the threaded drive and thereby cause a longitudinal adjustment of the at least one tensioning means. By way of example, the actuation means can be embodied as a hand wheel arranged on a handgrip or as a motor arranged in a handgrip. The actuation means can generate a rotational movement of the torsion shaft. The torsion shaft, in particular, is elongate and continuous from the proximal to the distal end region of the first shank portion and has a flexible design, at least in portions thereof. The torsion shaft can, inside the first shank portion, be guided in an edge region of the cross section in such a way that a sufficient cross-sectional area remains for passing through further channels or electrical and optical lines. The rotation of the at least one torsion shaft coupled to the at least one threaded drive can therefore control the longitudinal adjustment of the tensioning means for controlling the angling of the second shank portion.

As a result of a threaded drive being provided for longitudinal adjustment of the tensioning means, it is possible to realize a precisely controllable angling of the second shank portion of the shank with sufficient force. Furthermore, a threaded drive has a simple construction, is robust and can be produced inexpensively. Furthermore, as a result of the threaded drive being drivable by at least one torsion shaft extending inside the first shank portion, an actuation movement for controlling the angling of the second shank portion can be transmitted in a simple manner by a shank designed with a small diameter. In particular, the actuation movement is transmitted more directly to the second shank portion than would be possible with cable pulls or Bowden cables. In the process, no pulling or pushing force is exerted on the first shank portion, which generally makes up the majority of the overall length of the shank, such that a compression of the shank is avoided. Moreover, re-tensioning of cable pulls, which could lengthen over time, is not required. Furthermore, the actuation movement transmitted as far as the second shank portion is largely independent of the length and the curvature of the first shank portion such that the controllability of angling the second shank portion is improved. In this manner, a flexible shank with a simple design, in particular, for a flexible endoscope or for a flexible endoscopic instrument is developed, in which a distal shank portion that can be angled can be controlled independently of a curvature of a proximal shank portion with actuation means arranged on the proximal side.

In accordance with a preferred embodiment of the invention, the at least one tensioning means is embodied as a cable pull, which is connected to a distal end of the torsion shaft by the threaded drive for controlling the longitudinal adjustment of said tensioning means. The cable pull is guided in a longitudinally displaceable manner inside the second shank portion and connected at its distal end to a distal end region of the second shank portion. The proximal end of the cable pull is connected to the threaded drive. The threaded drive can be arranged in a proximal end region of the second shank portion, in a distal end region of the first shank portion, overarching in both shank portions or in a transition portion between the first and the second shank portion. The transition portion need not necessarily have a flexible design. As a result of there being an angling of the second shank portion by means of a longitudinal adjustment of a cable pull, the proximal end of which can be displaced in the longitudinal direction by the threaded drive, the angling of the second shank portion can be brought about in a particularly simple and effective manner.

The threaded drive preferably comprises a threaded rod, which cooperates with a threaded nut, connected to the distal end of the torsion shaft for rotation therewith, for the purposes of longitudinal adjustment of the cable pull. The nut is placed onto the threaded rod and has a female thread cooperating with the male thread on the threaded rod. As a result of rotating the nut relative to the threaded rod, the nut and the threaded rod can be displaced relative to one another in the longitudinal direction. In particular, the threaded drive is arranged in the distal end region of the first shank portion. The distal end region of the first shank portion can have a rigid or a flexible design. The threaded rod can be flexible, but preferably has a rigid design. Such a threaded drive comprising, in particular, only one threaded rod and only a single nut cooperating therewith has a simple design and is robust and enables a precise control of the angling of the second shank portion.

In a particularly advantageous manner, the threaded rod is longitudinally displaceable in the distal end region of the first shank portion, but guided secured against rotation and connected with the distal end thereof to the proximal end of the cable pull guided inside the second shank portion. Here, the nut is connected to the distal end of the torsion shaft for rotation therewith and rotatably mounted in the distal end region of the first shank portion and supported in the longitudinal direction. A rotation of the torsion shaft in a first direction leads to a movement of the proximal end of the cable pull in the proximal direction and to a corresponding angling of the second shank portion, while a rotation of the torsion shaft in the opposite direction brings about a movement of the proximal end of the cable pull in the distal direction and hence enables a reduction in the angling or angling in the opposite direction. As a result of this, a conversion of the rotational movement of the torsion shaft into a longitudinal adjustment of the cable pull for controlling the angling of the second shank portion is possible in a particularly simple manner.

In accordance with a further preferred embodiment of the invention, the tensioning means, or at least potions thereof, is/are itself/themselves embodied as a threaded rod, which is flexible at least in portions, of the at least one threaded drive. The threaded rod is therefore guided in a longitudinally displaceable manner inside the second shank portion and connected to a distal end region of the second shank portion, preferably only connected to a distal end region of the second shank portion.

The threaded rod is, in particular, mounted in a rotationally secured manner in the shank and cooperates with a threaded nut which is connected to the distal end of the torsion shaft for rotation therewith. The threaded nut, which is mounted rotatably with the torsion shaft and can be driven by the latter, but is supported against a longitudinal displacement relative to the endoscope shank, is put onto a proximal end region of the threaded rod. As a result of a rotation of the torsion shaft, the nut therefore rotates relative to the threaded rod, as a result of which the proximal end region of the threaded rod is displaced in the longitudinal direction. As a result, the effective length of the tensioning means formed at least in portions by the threaded rod and guided in the second shank portion is changed and hence a longitudinal adjustment of the tensioning means is brought about. Such a threaded drive comprises only one threaded rod and only a single nut cooperating therewith and therefore has a particularly simple embodiment, wherein furthermore a cable pull for angling the second shank portion can be dispensed with. As a result of this, controlling the angling of the second shank portion is enabled in a particularly simple manner by a rotation of the torsion shaft.

The second shank portion preferably has a plurality of tensioning means, which lie opposite to one another in pairs. Hence, when the second shank portion is angled, two tensioning means respectively act against one another, wherein the respective longitudinal adjustments of the tensioning means are directed against one another. As a result of this, angling in different directions can be obtained with a particularly high accuracy and always with sufficient force since one of the tensioning means is shortened or the distal end of one of the tensioning means is pulled in the proximal direction in each angling direction.

In particular, provision can be made for two pairs of tensioning means offset by 90° with respect to one another in relation to a longitudinal axis of the second shank portion in order to enable angling of the second shank portion in mutually perpendicular directions. As a result of this, as seen by a user, angling left or right and also up or down as well as, by simultaneous actuation of the pairs of tensioning means, angling in every direction situated therebetween is possible in a particularly simple manner.

Alternatively, it is possible, for example, to provide three tensioning means offset in each case by approximately 120° in relation to the longitudinal axis. This can also achieve angling in all directions.

Advantageously, a plurality of torsion shafts are provided, which cooperate with the plurality of tensioning means for controlling angling of the second shank portion. In particular, each torsion shaft can be connected to respectively one tensioning means or respectively one threaded drive. As a result of this, angling of the second shank portion in different directions is made possible with particularly high accuracy in a simple manner.

In accordance with a preferred embodiment of the invention, the plurality of torsion shafts are connected to one another by a toothed gear such that tensioning means lying opposite to one another can in each case be moved in opposite directions. In particular, the toothed gear can be arranged at a proximal end of the torsion shaft, wherein in each case torsion shafts associated with two threaded drives lying opposite to one another are coupled to one another. The toothed gear renders such coupling possible that a lengthening of a tensioning means leads to simultaneous shortening of a tensioning means lying opposite and acting counter to the former or a displacement of a tensioning means in the proximal direction leads to a displacement of a tensioning means lying opposite and acting counter to the former in the distal direction. By way of example, to this end each of the two torsion shafts counteracting one another can carry a toothed wheel in a rotationally secured manner at the proximal end thereof, wherein the two toothed wheels mesh with one another such that the torsion shafts always rotate in opposite directions and the respective threaded drives, which in this case can have the same design, are driven in opposite directions and cause opposite longitudinal adjustments of the tensioning means. If the two corresponding threaded drives have different thread directions, i.e. a left-handed thread and a right-handed thread, an odd number of toothed wheels can be inserted between the two toothed wheels connected to the torsion shafts such that the two torsion shafts rotate in the same direction and cause counteracting length changes of the tensioning means by the different threaded drives. As a result of this, the operability and controllability of angling the second shank portion are further improved.

Advantageously, the at least one threaded drive, in particular a threaded rod of the threaded drive, has a constant thread pitch. As a result of this, a linear relationship is rendered possible between, on the one hand, the rotational angle or the number of rotations of the torsion shaft and, on the other hand, the longitudinal adjustment of the tensioning means and hence the angling of the second shank portion caused thereby. Furthermore, this can achieve low-tension counteraction of threaded drives lying opposite to one another and the thereby coupled torsion shafts for angling the second shank portion in different directions. A small thread pitch of the threaded drive in this case allows particularly sensitive control of the angling while a larger thread pitch enables particularly fast adjustment of the angling with relatively few rotations of the torsion shaft.

An endoscope according to the invention comprises an above-described shank, which is embodied as an endoscope shank. In particular, optical waveguides, image guides, suction or flushing channels and/or one or more working channels for endoscopic work instruments can extend through the shank.

An endoscopic instrument according to the invention comprises an elongate shank, which has a design as described above. Furthermore, arranged at the distal end of the shank of the endoscopic instrument there can be a tool, which can be operated from the proximal end of the shank, for example with the aid of grips arranged at the proximal end, by means of a transmission means, e.g. a tensioning element, extending inside the shank. By way of example, the shank of the endoscopic instrument can comprise suction or flushing channels, as well as a working channel through which an endoscopic work instrument that cannot be actively controlled can be inserted.

The flexible endoscope or the flexible endoscopic instrument is preferably embodied such that the at least one torsion shaft can be actuated by at least one operating element, which can be embodied as e.g. a hand wheel, lever or crank and is arranged in a proximal region of the endoscope or the endoscopic instrument, in particular on a handgrip, and/or by a motor, which can for example be arranged in the handgrip. The torsion shaft can be put into sufficient rotation for a precise control of the angling by means of both the operating element and the motor. However, the motor can, for example, also be arranged in a motor unit separate from the endoscope or endoscopic instrument and also, optionally, from the handgrip, wherein the rotational movement can be transmitted to the endoscope shank via a flexible shaft. The actuation by a motor which can be actuated by a control apparatus is, in particular, also advantageous if the tensioning means are arranged not lying opposite to one another in pairs but rather offset from one another by, for example, 120°.

In accordance with a further preferred embodiment of the invention, the flexible endoscope or the flexible endoscopic instrument comprises a handle, in particular a handgrip, wherein the shank is detachably connectable to the handle via a coupling. An endoscopic system can therefore comprise a plurality of shanks with different dimensions, in particular different diameters and lengths, and possibly with different designs, which can be connected to a handle, which can for example comprise the drive for the angling and a camera. As a result of there being no need to connect cable pulls extending in the longitudinal direction of the shank with the handle when coupling the shank to the handle, there is no need to readjust or tension these after coupling. Compared to this, a simpler connection, which merely needs to have a rotationally secured design and can be easy to separate in the longitudinal direction, is enabled as a result of transmitting the actuation movement to the drive of the threaded drive by a torsion shaft. The drive and a control apparatus are arranged in the handle. This creates an endoscope or an endoscopic instrument and/or an endoscopic system, which can be used in a particularly versatile manner but is relatively inexpensive due to the handle being able to be used with a plurality of shanks and requires little operational outlay when changing the shanks.

In a particularly preferred manner, the handle comprises a motor-driven drive of the at least one torsion shaft or threaded drive. When decoupling the shank from the handle, a rotary position of the at least one torsion shaft is stored and a torsion shaft coupling of the handle can be actuated for coupling on the shank such that said handle, when being coupled on, assumes a rotary position corresponding to the stored rotational position of the torsion shaft. This enables particularly simple coupling of the shank to the handle. Furthermore, storing the rotational position of the torsion shaft enables a particularly precise control of the angling of the second shank portion. As a result of the rotational position of the torsion shaft, a respectively current rotational position of a threaded drive can be established and hence it is possible to precisely control the angling. As a result of this, the control apparatus can also establish the respectively current angling position of the second shank portion such that, in the case of e.g. a virtual display of the endoscope or the endoscopic instrument and the observed cavity, the spatial position of the endoscope tip can be displayed correctly.

The rotary position of the at least one torsion shaft, which the latter assumes when being separated from the corresponding motor shaft, can advantageously be stored in a storage medium associated with the shank. What this can achieve is that the coupling of the motor shaft can be rotated into the correct position when connecting the shank to a handle and the control apparatus has the required information for precise control of the angling, even in the case where the shank is connected to a different handle.

In order to establish the rotary position of the torsion shaft during separation from the handle, provision can be made for a sensor, for example a potentiometer or another rotary encoder, in particular an absolute encoder, for example an optical multi-turn rotary encoder, which, in particular, is arranged in a proximal end region of the shank. The sensor measures the rotations and the angular distance covered by the torsion shaft; in the case of separation from the drive, the sensor can remain in the corresponding rotational position such that read out is possible at all times. In this manner, the rotations carried out during operation of the endoscope or the endoscopic instrument for angling the second shank portion can be counted and the rotary position of the torsion shaft can be established.

Hence, when using an endoscope according to the invention or an endoscopic instrument according to the invention, a torsion shaft in particular, extending in a first shank portion arranged on the proximal side, is rotated with the aid of an operating element or by a motor in order to control a shank portion that can be angled, in particular a tip of the endoscope that can be angled, or to control the working direction of a tool arranged at the tip of the endoscopic instrument and as a result of this a tensioning means extending in a second portion of the shank is adjusted in the longitudinal direction thereof, i.e. shortened or lengthened or displaced. The second shank portion is curved by the longitudinal adjustment of the tensioning means and the endoscope tip or the tip of the endoscopic instrument is angled in this manner.

If a different endoscope shank should be used with the same handle of the flexible endoscope or the same shank should be used with a different handle, the shank connected to the handle is separated from the latter; since the torsion shaft only needs to be connected in a rotationally secured manner to a motor shaft associated with the handle, this is possible in a particularly simple manner. A corresponding statement applies to the shank and the handle of a flexible endoscopic instrument. The rotation of the torsion shaft can be established by a sensor and, when the shank is separated from the handle, this can be stored in a storage medium arranged in the proximal end region of the shank. When another shank is connected to the handle or another handle is connected to the shank, the rotary position stored in the storage medium of the shank to be connected is read out, e.g. electrically, mechanically or else by wireless transmission means, and the motor shaft is brought into a suitable position such that the connection can be established in a simple manner. Furthermore, the readout of the rotary position enables a calculation of the current position and a precise control of the endoscope tip or the tip of the endoscopic instrument.

A flexible threaded rod, which, in particular, is suitable for use in an above-described threaded drive, can for example be produced by welding a helically coiled wire onto a flexible wire. Here, the cross section of the coiled wire corresponds to the desired thread profile, while the pitch of the coil corresponds to the thread pitch. Here, for example, a triangular cross-sectional area can be particularly advantageous, as a result of which, firstly, secure attachment on the flexible wire is made possible and, secondly, a thread with advantageous properties is produced. The coiled wire can already be helically coiled prior to being welded on or else only be coiled by welding. Instead of welding, other connection types, such as soldering or adhesive bonding, are also possible. As a result, a flexible threaded rod with a small diameter and a desired pitch and a desired thread profile can be produced in a simple and inexpensive manner.

It is understood that the features mentioned above and the features yet to be explained below can be used not only in the respectively specified combination, but also in other combinations or on their own, without departing from the scope of the present invention

BRIEF DESCRIPTION OF THE DRAWINGS

Further aspects of the invention emerge from the following description of a preferred exemplary embodiment and the attached drawings. In detail.

DETAILED DESCRIPTION OF THE INVENTION

Figure 1A:
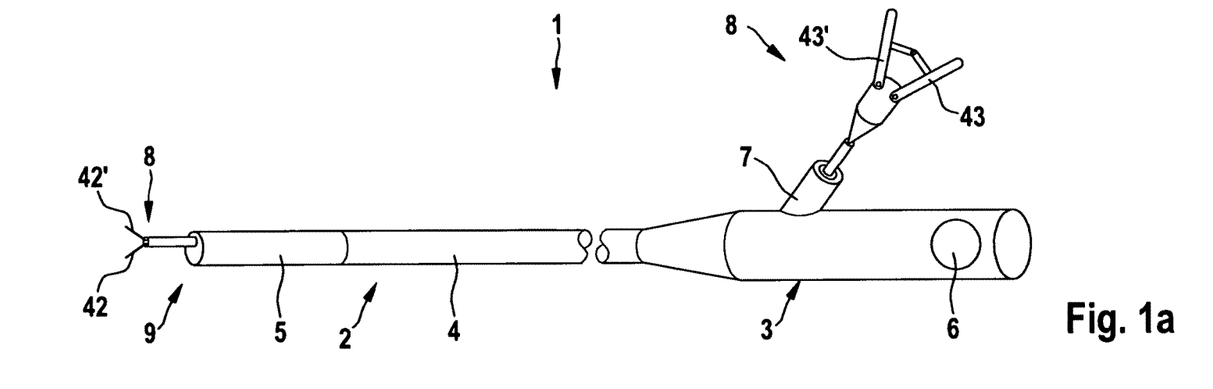
FIGS. 1A AND 1B show, in an overview, a flexible endoscope according to the invention in accordance with one exemplary embodiment.
Figure 1B:
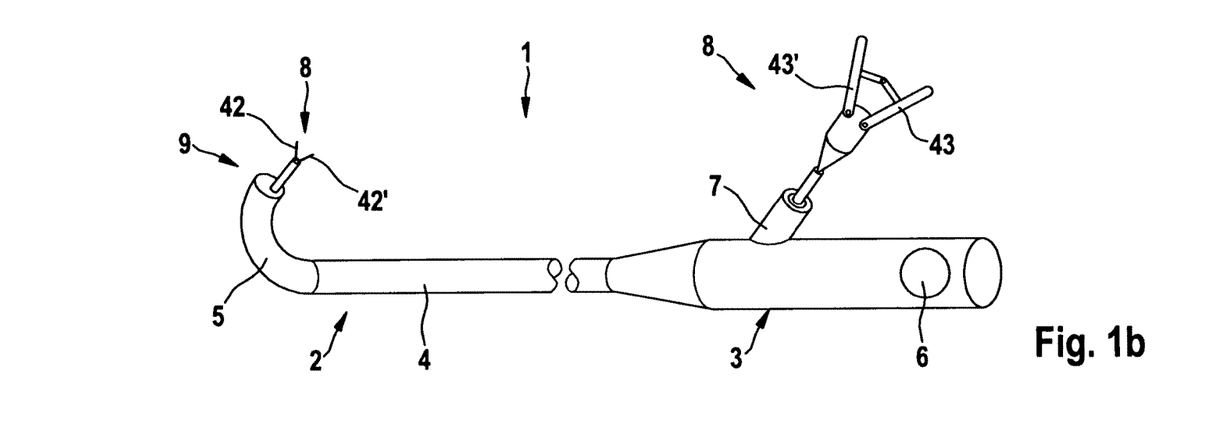

As depicted in FIGS. 1a and 1b, a flexible endoscope 1 according to the invention comprises a flexible endoscope shank 2 and a handgrip 3 in accordance with one exemplary embodiment of the invention. The endoscope shank 2 comprises a first shank portion 4 and a second shank portion 5. The second shank portion 5 is the distal end portion of the endoscope shank 2, while the first shank portion 4 is the proximal part of the endoscope shank 2, which, in the shown example, takes up the whole remaining length of the endoscope shank 2 and is significantly longer than the second shank portion 5. A symbolically depicted operating element 6 for controlling angling of the second shank portion 5 is arranged on the handgrip 3. By way of example, the operating element 6 can be embodied as a hand wheel, lever or crank, but can also, for example, be an operating element for actuating a motor. Furthermore, the handgrip 3 has a guide tube 7, into which an endoscopic work instrument 8, which is depicted in an exemplary fashion and not controllable according to the invention, can be inserted and guided through a working channel extending inside the endoscope shank 2 as far as the distal end 9 of the endoscope shank 2 and beyond. At the distal end thereof, the work instrument 8 has a tool, e.g. embodied for gripping or cutting, with two jaw parts 42, 42', acting against one another, which can be actuated by grips 43, 43' arranged on the proximal side.

In FIG. 1a, the endoscope shank 2 is depicted in a stretched state, while FIG. 1b shows the endoscope 1 from FIG. 1a in an angled state. The instrument 8 and the first shank portion 4 have a flexible design, but cannot be actively controlled. By contrast, the second shank portion 5 of the endoscope shank 2 can be actively curved by actuating the operating element 6 and hence it can be controlled. In its interior, the second shank portion 5 has a support structure made of shank segments connected to one another in a hinged fashion, which, for angling purposes, cooperate with at least two tensioning means that lie opposite to one another and are guided inside the second shank portion 5. Each tensioning means is in each case connected to the handgrip 3 and the operating element 6 by a torsion shaft, which extends through the first shank portion 4. By means of a coupling, the endoscope shank 2 can be separated from the handgrip 3 and can be reconnected to the latter (not illustrated).

In portions, the endoscope shank 2 can be strengthened by a surrounding metal mesh. The first shank portion 4 and the second shank portion 5 can be surrounded by a flexible sleeve, which, for example, can be tubing made of plastic material. The distal end region of the second shank portion 5 can have a rigid design and receive optical and electronic components, for example an endoscope lens and optionally an electronic image recorder (not illustrated).

In accordance with one exemplary embodiment, a flexible endoscopic instrument according to the invention has the same design as the flexible endoscope 1 depicted in FIGS. 1a and 1b, but does not have an optical unit. The flexible endoscopic instrument can comprise the endoscopic work instrument 8 or else be designed as endoscopic guide instrument for guiding and controlling an endoscopic work instrument 8 that cannot be controlled.

Figure 2:
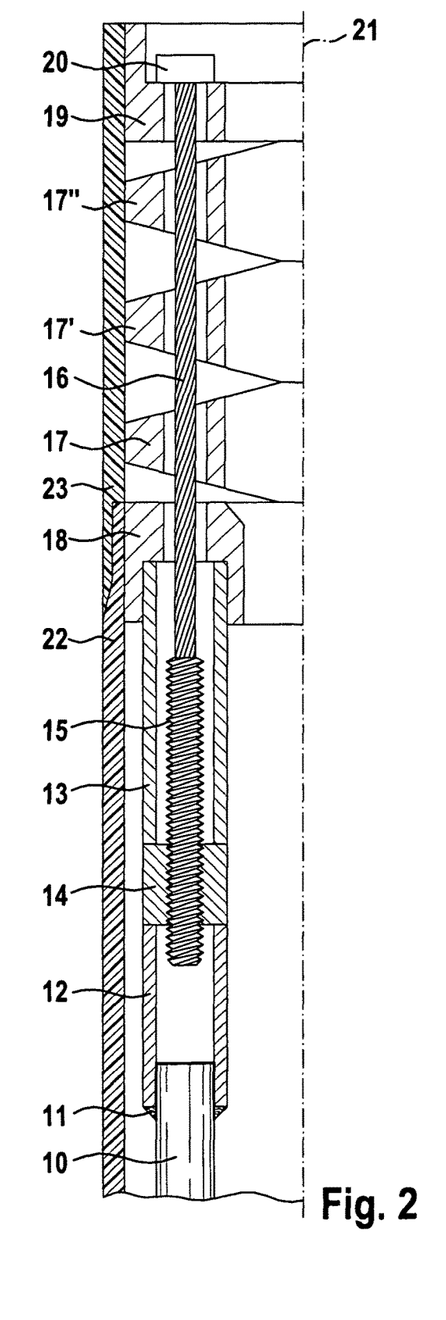
FIG. 2 shows a schematic longitudinal section through an end region of a shank in accordance with a first exemplary embodiment of the invention, with only one half of the longitudinal section being depicted.

FIG. 2 depicts the longitudinal section of an embodiment of the invention with a tensioning means, embodied as a cable pull, of the second shank portion 5 of the endoscope shank 2 (see FIG. 1), which is connected to the torsion shaft 10 arranged in the first shank portion 4 by a threaded drive, with only the half of the longitudinal section lying on one side of the longitudinal axis 21 being shown. At its proximal end, the torsion shaft 10 can, for example, be driven by motor, in particular be driven in a rotary manner by an electric motor arranged in a handgrip (not illustrated). The torsion shaft 10 is elongate, thin and as rigid as possible in respect of rotation. By way of example, the torsion shaft 10 can be made of nitinol. By way of example, the torsion shaft 10 can be embodied as a thin, flexible pipe. At the distal end of the torsion shaft 10, the latter is securely connected to a sleeve 12, for example with the aid of an adhesive 11, which fills an annular gap and a hollow, which are formed by the sleeve 12 with the torsion shaft 10. The sleeve 12 is rotatably mounted inside the first shank portion 4 and is supported by a guide 13 against longitudinal displacement, particularly in the distal direction. At its distal end region, the sleeve 12 is fixedly connected to a nut 14, which moves on a threaded rod 15, wherein a female thread of the nut 14 meshes with a male thread of the threaded rod 15. The threaded rod 15 is mounted in a longitudinally displaceable manner and can be secured against rotation by the guide 13 and/or by the wire pull 16, which is described below and can have a largely rigid design in respect of rotation, and by the holder 20 mounted in a rotationally secured manner in the end segment 19. The threaded rod 15 is relatively short, for example has a length of 15 mm, and has a rigid design. The threaded drive, which is formed by the sleeve 12 with the nut 14, the guide 13 and the threaded rod 15, is arranged in a distal end region of the first shank portion 4. Without substantial restriction in the functionality of the endoscope, said threaded drive can be designed to be rigid or with slight flexibility, as a result of which a simple design of the threaded drive is made possible.

The threaded rod 15 has a tension-resistant connection to a wire pull 16 and is preferably connected for rotation therewith, which wire pull is guided in an edge region of the second shank portion 5. The second shank portion 5 has a support structure, of which three segments 17, 17', 17" and a proximal end segment 18 and a distal end segment 19 are depicted symbolically in FIG. 2. The guide 13 of the threaded drive is affixed or mounted in the proximal end segment 18. At the distal end segment 19, the wire pull 16 is held in a tension-resistant manner and preferably also in a rotationally secured manner by a holder 20. The distal end segment 19 can have further components, for example an endoscope lens and/or outputs of channels extending inside the endoscope shank. In the edge region of the segments 18, 17, 17', 17", 19, the wire pull 16 is guided through appropriate openings or bores in a longitudinally displaceable manner. It is possible to identify in FIG. 2 that the holder 20 of the wire pull 16 is radially offset in relation to a longitudinal axis 21 of the second shank portion 5 and therefore also in relation to the pivot axes, by means of which the segments 18, 17, 17', 17", 19 are mounted such that they can pivot with respect to one another and of which for example alternately one is substantially perpendicular to the longitudinal axis 21 and intersects the latter and the pivot axes of the respectively adjacent segments are perpendicular thereto such that the pivot axes directed in different directions enable angling in all directions.

If the torsion shaft 10 is now made to rotate by the motor not depicted in FIG. 2, the nut 14 is carried along by the sleeve 12 and rotated in respect of the distal threaded rod 15, which is guided in a rotationally secured manner in the endoscope shank. During a rotation in a first rotational direction, the threaded rod 15 is displaced in the proximal direction; the proximal end of the threaded rod 15 is then held in the sleeve 12 such that it is arranged on the proximal side of the nut 14. In the process, the wire pull 16 is displaced in the proximal direction in relation to the proximal end segment 18. As a result of the off-axis arrangement of the holder 20, this causes a tilt of the distal end segment 19 and, depending on the embodiment of the hinged connection between the segments 18, 17, 17', 17", 19, also a corresponding tilt of the segments 17, 17', 17". As a result of this, the second shank portion 5 is curved and this brings about angling of the second shank portion 5 or the endoscope tip formed by the distal end segment 19.

A rotation of the torsion shaft 10 in the opposite direction leads to a displacement of the threaded rod 15 in the distal direction and hence to a relaxation of the wire pull 16. If a further, similar mechanism as depicted in FIG. 2 is arranged on the side of the endoscope shank lying radially opposite to the side depicted in FIG. 2, angling of the second shank portion 5 can be effected in the opposite direction, which is followed by the wire pull 16, by a rotation of the torsion shaft arranged on the opposite side. To the extent that the holder 20, the wire pull 16 and the guide of the wire pull 16 have a corresponding embodiment in the shank segments 18, 17, 17', 17", 19, it is also possible to exert a pushing force for angling the second shank portion 5 in the opposite direction. In order to enable angling of the second shank portion 5 in all directions, provision can be made for four threaded drives, acting against one another in pairs, which each have a torsion shaft 10 and which are in each case offset by 90° with respect to one another in relation to the longitudinal axis 21. FIG. 2 also indicates an outer sleeve 22, which surrounds the first shank portion 4, and the outer sleeve 23, which is connected to said outer sleeve 22 and surrounds the second shank portion 5.

Figure 3:
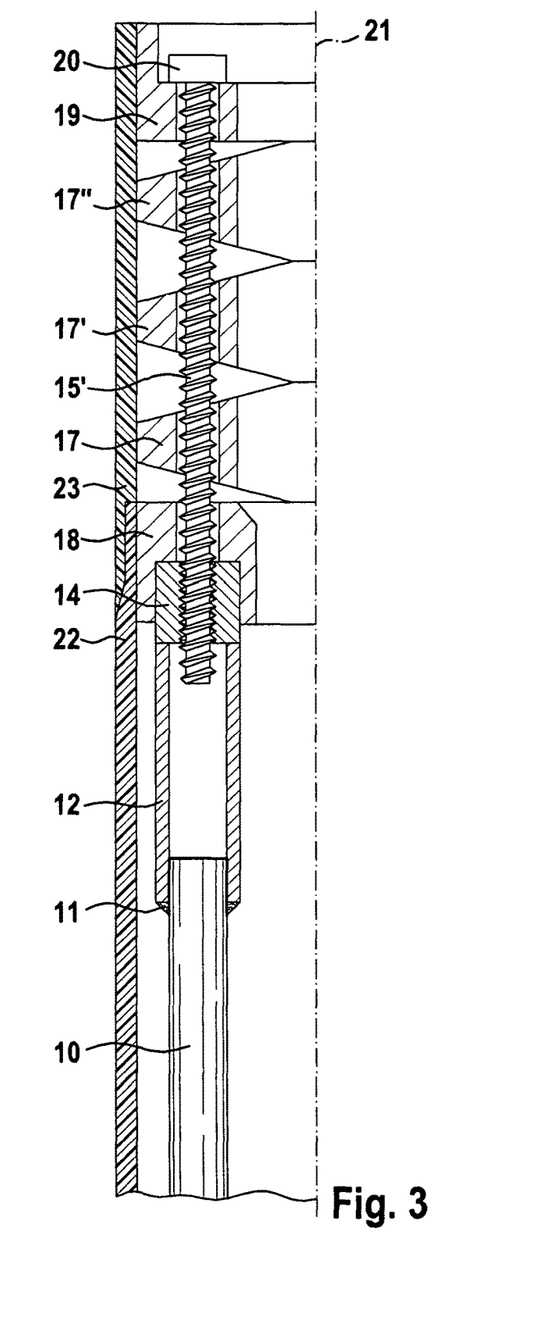
FIG. 3 shows a schematic longitudinal section through an end region of a shank in accordance with a second exemplary embodiment of the invention, with only one half of the longitudinal section being depicted.

FIG. 3 likewise depicts, in a longitudinal section of one half, an embodiment of the invention, in which a wire pull for effecting the angling of the second shank portion 5 is not required, but in which a flexible threaded rod 15', which is guided in the second shank portion 5, is provided instead of the wire pull. As described in relation to FIG. 2, a torsion shaft 10, which can be driven at its proximal end by e.g. an electric motor, extends inside the first shank portion 4. Connected to the torsion shaft 10 by means of the adhesive 11 is a rotatable sleeve 12, which is fixedly connected to a nut 14 at the distal end region thereof. The nut 14 is mounted in a rotatable but, at least in the distal direction, not a longitudinally displaceable manner in a proximal end segment 18 of the second shank portion 5. The female thread of the nut 14 meshes with the male thread of the flexible threaded rod 15'. The threaded rod 15' is guided in a longitudinally displaceable manner in the openings or bores in the edge regions of the shank segments 17, 17', 17" and the proximal end segment 18. The threaded rod 15' can be guided in a flexible sleeve. With the distal end thereof, the threaded rod 15' is held in a rotationally secured and tension-resistant manner in a holder 20 at the distal end segment 19.

As a result of a rotation of the nut 14 due to a rotation of the torsion shaft 10, the threaded rod 15' is displaced in a proximal or distal direction with the proximal end region thereof, depending on the rotational direction. As a result of this, a pull or a push force is exerted on the distal end segment, whereby the off-axis guidance of the threaded rod 15' causes a corresponding angling of the second shank portion 5. A mechanism with a similar design arranged on the radially opposite side can act against the threaded rod 15' such that angling in any direction can be effected even by pull forces alone. The embodiment depicted in FIG. 3, in which the tensioning means itself is embodied as threaded rod 15' or in which the threaded rod 15' itself acts as a wire pull, therefore works in a similar manner to the one depicted in FIG. 2, but can make do without a separate cable pull and therefore has a particularly simple design.

Figure 4:
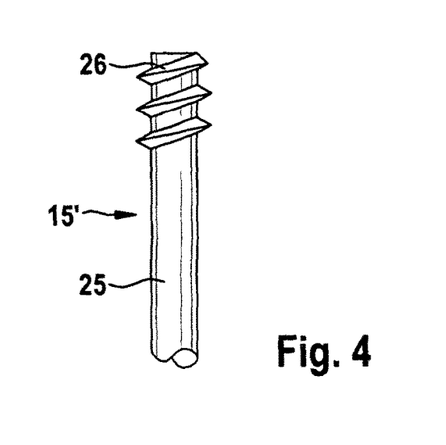
FIG. 4 shows a flexible threaded rod in accordance with an exemplary embodiment which has only been partially provided with a thread.

FIG. 4 shows a flexible threaded rod 15', which is, in particular, suitable for use in an embodiment in accordance with FIG. 3, in a state which has only been partly provided with a thread in accordance with a production method described in an exemplary manner. Such a flexible threaded rod 15' can be produced by welding a wire 26 on to a flexible wire 25. Here, the cross section of the welded-on wire 26 corresponds to the desired thread profile, for example a triangular profile. During welding, the wire 26 is fixed with a flat side on the wire 25 with a helical shape, wherein the pitch of the helix provides the thread pitch of the threaded rod 15'. Pitch and profile of the female thread of the nut 14 are thus adapted to the male thread of the threaded rod 15' produced in this manner.

Figure 5:
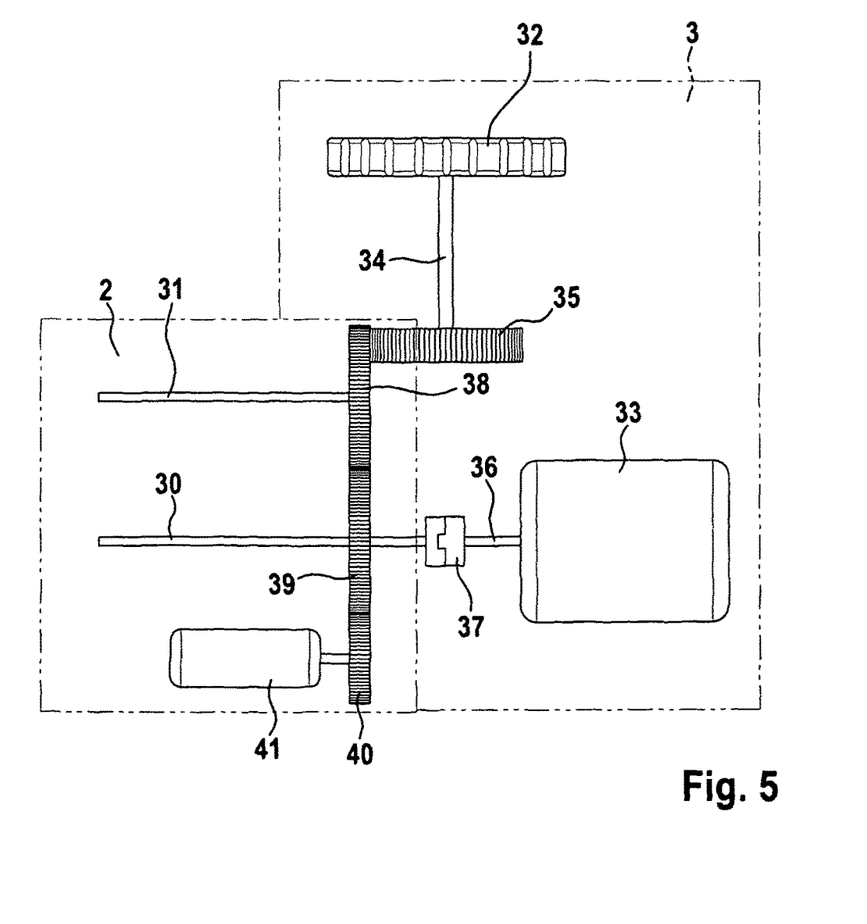
FIG. 5 shows a schematic depiction of a coupling mechanism between an endoscope shank and a handle in accordance with one exemplary embodiment of the invention.

As depicted symbolically in FIG. 5, an endoscope shank 2 can have a first and a second torsion shaft 30, 31, which can be driven by both a hand wheel 32 and a motor 33. The hand wheel 32 is connected to a toothed wheel 35 via a shaft 34; here, provision can be made for a speed reduction (not depicted in FIG. 4), as a result of which, for example, one rotation of the hand wheel causes 5 to 10 rotations of the torsion shafts. The motor 33 drives a motor shaft 36, which has a coupling 37. By way of example, the coupling can be embodied as a slipping coupling, magnetic coupling, auxiliary drive or in another manner known per se. Hand wheel 32 and motor 33, as well as the shafts 34 and 36, the toothed wheel 35 and the coupling 37 are associated with a handgrip 3, which can be attached to the endoscope shank 2.

When attached to the endoscope shank 2, the toothed wheel 35 meshes with a toothed wheel 38 connected to the torsion shaft 31 for rotation therewith and driving the latter. The torsion shaft 30 is driven directly by the coupling 37. The toothed wheel 38 meshes with the toothed wheel 39, which sits on the torsion shaft 30 for rotation therewith and in turn drives the toothed wheel 40, which is connected to a rotary encoder 41. The relative rotation of the torsion shafts 30, 31 is defined by the connection of the toothed wheels 38, 39. Here, the threaded rods of the threaded drives driven by the torsion shafts 30, 31 have pitches in the same sense such that, if there is a shortening on one side of the second shank portion 5, a corresponding lengthening is brought about on the other side of the second shank portion 5. The rotary encoder 41 registers the rotation of the toothed wheel 40, from which a rotational position of the torsion shafts 30, 31 can be established. This rotational position is stored in a storage device (not depicted) and, when the shank 2 is coupled to the handgrip 3, this is transmitted to a control apparatus (likewise not depicted) of the motor 33. As a result of this, actuation of the motor 33 corresponding to the actual position of the drives can be achieved at any time.

For the sake of clarity, not all the reference signs are shown in all of the figures. Reference signs not explained in connection with one figure have the same meaning as in the other figures.

The invention claimed is:

1. A shank for a flexible endoscope or for a flexible endoscopic instrument, comprising:
    a first shank portion;
    a second shank portion arranged in a distal direction from the first shank portion;
    wherein the second shank portion can be angled relative to a distal end region of the first shank portion by a longitudinal adjustment of at least one tensioning means which is guided in a longitudinally displaceable manner inside the second shank portion and connected to a distal end region of the second shank portion;
    at least one threaded drive for the longitudinal adjustment of the at least one tensioning means, which is driven by at least one torsion shaft extending inside the first shank portion.

2. The shank as claimed in claim 1, wherein the at least one tensioning means is embodied as a cable pull and connected to a distal end of the torsion shaft by the threaded drive.

3. The shank as claimed in claim 2, wherein the threaded drive comprises a threaded rod, which, for longitudinal adjustment of the cable pull, cooperates with a nut connected to the distal end of the torsion shaft for rotation therewith.

4. The shank as claimed in claim 3, wherein the threaded rod is connected to a proximal end of the cable pull and mounted in a longitudinally displaceable and rotationally secured manner in the distal end region of the first shank portion.

5. The shank as claimed in claim 1, wherein the at least one tensioning means is embodied as a threaded rod, which is flexible at least in portions, of the at least one threaded drive, the threaded rod cooperating with a nut connected to the distal end of the torsion shaft for rotation therewith for longitudinal adjustment of the flexible threaded rod.

6. The shank as claimed in claim 1, wherein the second shank portion has a plurality of tensioning means, which lie opposite to one another in pairs.

7. The shank as claimed in claim 6, wherein the first shank portion has a plurality of torsion shafts, which cooperate with the plurality of tensioning means for controlling angling in different directions.

8. The shank as claimed in claim 7, wherein the plurality of torsion shafts are connected to one another by at least one toothed gear such that tensioning means lying opposite to one another can be longitudinally adjusted in opposite senses.

9. A flexible endoscope with a shank comprising
    a first shank portion;
    a second shank portion arranged in a distal direction from the first shank portion;
    wherein the second shank portion can be angled relative to a distal end region of the first shank portion by a longitudinal adjustment of at least one tensioning means which is guided in a longitudinally displaceable manner inside the second shank portion and connected to a distal end region of the second shank portion;
    at least one threaded drive for the longitudinal adjustment of the at least one tensioning means, which is driven by at least one torsion shaft extending inside the first shank portion.

10. A flexible endoscopic instrument with a shank comprising:

a first shank portion;

a second shank portion arranged in a distal direction from the first shank portion, a second shank portion;

wherein the second shank portion can be angled relative to a distal end region of the first shank portion by a longitudinal adjustment of at least one tensioning means which is guided in a longitudinally displaceable manner inside the second shank portion and connected to a distal end region of the second shank portion;

at least one threaded drive for the longitudinal adjustment of the at least one tensioning means, which is driven by at least one torsion shaft extending inside the first shank portion.

11. The flexible endoscope as claimed in claim 9, wherein the torsion shaft can be actuated by at least one operating element arranged on the proximal side of the first shank portion and/or by a motor arranged on the proximal side of the first shank portion.

12. The flexible endoscope as claimed in claim 9, wherein the flexible endoscope comprises a handle arranged on the proximal side of the first shank portion and wherein the shank is detachably connectable to the handle.

13. The flexible endoscope as claimed in claim 12, wherein the handle is associated with a motor-driven drive of the at least one torsion shaft, wherein a rotary position of the at least one torsion shaft can be stored when separating the shank from the handle and wherein a torsion shaft coupling of the handle can be actuated accordingly for coupling on the shank.

14. The flexible endoscope as claimed in claim 13, wherein the rotary position of the at least one torsion shaft can be stored in a storage medium associated with the shank.

15. The flexible endoscope as claimed in claim 13, wherein a potentiometer or a rotary encoder is provided for establishing the rotary position.

16. The flexible endoscopic instrument as claimed in claim 10, wherein the torsion shaft can be actuated by at least one operating element arranged on the proximal side of the first shank portion and/or by a motor arranged on the proximal side of the first shank portion.

17. The flexible endoscopic instrument as claimed in claim 10, wherein the flexible endoscopic instrument comprises a handle arranged on the proximal side of the first shank portion and wherein the shank is detachably connectable to the handle.

18. The flexible endoscopic instrument as claimed in claim 17, wherein the handle is associated with a motor-driven drive of the at least one torsion shaft, wherein a rotary position of the at least one torsion shaft can be stored when separating the shank from the handle and wherein a torsion shaft coupling of the handle can be actuated accordingly for coupling on the shank.

19. The flexible endoscopic instrument as claimed in claim 18, wherein the rotary position of the at least one torsion shaft can be stored in a storage medium associated with the shank.

20. The flexible endoscopic instrument as claimed in claim 18, wherein a potentiometer or a rotary encoder is provided for establishing the rotary position.

* * * * *

UNITED STATES PATENT AND TRADEMARK OFFICE
CERTIFICATE OF CORRECTION

PATENT NO. : 10,206,560 B2
APPLICATION NO. : 14/013366
DATED : February 19, 2019
INVENTOR(S) : Gereon Kindler Page 1 of 1

It is certified that error appears in the above-identified patent and that said Letters Patent is hereby corrected as shown below:

On the Title Page

Column 1, (54) Title:
"Shank For A Flexible Endoscope Or A Flexible Endoscopic Instrument"

Should read:
--Shaft For A Flexible Endoscope Or A Flexible Endoscopic Instrument--

Signed and Sealed this
Twenty-sixth Day of March, 2019

Andrei Iancu
*Director of the United States Patent and Trademark Office*